United States Patent
Dobler

(10) Patent No.: US 10,874,192 B2
(45) Date of Patent: *Dec. 29, 2020

(54) FRAGRANCE SAMPLER INSERT

(75) Inventor: Sven Dobler, Huntington, NY (US)

(73) Assignee: Orlandi, Inc., Farmingdale, NY (US)

( * ) Notice: Subject to any disclaimer, the term of this patent is extended or adjusted under 35 U.S.C. 154(b) by 4567 days.

This patent is subject to a terminal disclaimer.

(21) Appl. No.: 10/986,123

(22) Filed: Nov. 10, 2004

(65) Prior Publication Data

US 2005/0061710 A1    Mar. 24, 2005

Related U.S. Application Data

(63) Continuation-in-part of application No. 10/464,392, filed on Jun. 17, 2003, now abandoned, which is a continuation-in-part of application No. 10/233,136, filed on Aug. 30, 2002, now Pat. No. 8,003,116, which is a continuation-in-part of application No. 09/858,566, filed on May 17, 2001, now Pat. No. 6,461,620, which is a continuation-in-part of application No. 09/531,296, filed on Mar. 20, 2000, now Pat. No. 6,251,408.

(51) Int. Cl.
| | |
|---|---|
| *A45D 40/00* | (2006.01) |
| *B65D 75/26* | (2006.01) |
| *B65D 43/16* | (2006.01) |
| *A61K 8/02* | (2006.01) |
| *A61L 9/12* | (2006.01) |
| *A61Q 13/00* | (2006.01) |
| *A45D 34/02* | (2006.01) |

(52) U.S. Cl.
CPC ............ *A45D 40/0087* (2013.01); *A61K 8/02* (2013.01); *A61L 9/12* (2013.01); *A61Q 13/00* (2013.01); *B65D 43/162* (2013.01); *B65D 75/26* (2013.01); *A45D 34/02* (2013.01); *A61K 2800/87* (2013.01)

(58) Field of Classification Search
None
See application file for complete search history.

(56) References Cited

U.S. PATENT DOCUMENTS

| | | |
|---|---|---|
| 4,155,500 A | 5/1979 | Dutcher |
| 4,208,012 A | 6/1980 | Dutcher |
| 4,279,373 A | 7/1981 | Montealegre |
| 4,280,649 A | 7/1981 | Montealegre |
| 4,301,095 A | 11/1981 | Mettler et al. |
| 4,484,768 A | 11/1984 | Norfleet |
| 4,487,801 A | 12/1984 | Turnbull et al. |
| 4,493,869 A | 1/1985 | Sweeny et al. |
| 4,606,956 A | 8/1986 | Charbonneau et al. |
| 4,615,486 A | 10/1986 | Konicek |
| 4,619,383 A | 10/1986 | Konicek |
| 4,661,388 A | 4/1987 | Charbonneau |
| 4,720,423 A | 1/1988 | Fraser |
| 4,751,934 A | 6/1988 | Moir et al. |
| 4,769,264 A | 9/1988 | Dreger |
| 4,809,912 A | 3/1989 | Santini |
| 4,848,378 A | 7/1989 | Moir et al. |
| 4,858,831 A | 8/1989 | Spector |
| 4,869,407 A | 9/1989 | Booth, Jr. et al. |
| 4,880,690 A | 11/1989 | Szycher et al. |
| 5,031,647 A * | 7/1991 | Seidler .................... 132/320 |
| 5,093,182 A | 3/1992 | Ross |
| 5,161,688 A | 10/1992 | Muchin |
| 5,192,380 A | 3/1993 | Hanada et al. |
| 5,192,386 A | 3/1993 | Moir et al. |
| 5,249,676 A | 10/1993 | Ashcraft et al. |
| 5,348,031 A * | 9/1994 | Cloud ...................... 132/317 |
| 5,391,420 A * | 2/1995 | Bootman et al. .......... 206/213.1 |
| 5,562,112 A | 10/1996 | Gunderman et al. |
| 5,566,693 A | 10/1996 | Gunderman et al. |
| 5,622,263 A * | 4/1997 | Greenland ................ 206/581 |
| 5,645,161 A | 7/1997 | Whitaker et al. |
| 5,690,130 A | 11/1997 | Gunderman et al. |
| 5,845,847 A | 12/1998 | Martin et al. |
| 5,879,769 A | 3/1999 | Greenland et al. |
| 5,899,382 A | 5/1999 | Hayes et al. |
| 6,006,916 A * | 12/1999 | Matsos et al. ................ 206/581 |
| 6,012,643 A | 1/2000 | Barlow et al. |
| 6,251,408 B1 * | 6/2001 | Dobler ........................ 424/400 |
| 6,305,531 B1 | 10/2001 | Wilkman |
| 6,461,620 B2 * | 10/2002 | Dobler ........................ 424/400 |
| 2002/0011424 A1 | 1/2002 | Wilkman |
| 2003/0010670 A1 | 1/2003 | Dobler |
| 2003/0106812 A1 | 6/2003 | Wilkman |

\* cited by examiner

*Primary Examiner* — Hasan S Ahmed
(74) *Attorney, Agent, or Firm* — Paul M Denk

(57) ABSTRACT

A fragrance sampler is provided which is made from a bottom ply and a top ply of material and an applicator. A cosmetic sample, such as a wet fragrance, is deposited on the bottom ply. An absorbent applicator attaches to the top ply. The applicator collects a portion from the sample and then applies the portion for testing. A well is formed in at least one of the plies and is sized and shaped to surround the sample. An applicator joins to the other ply and fits within the well. The two plies are then adhered together to form a liquid tight seal between the plies and around the well.

1 Claim, 8 Drawing Sheets

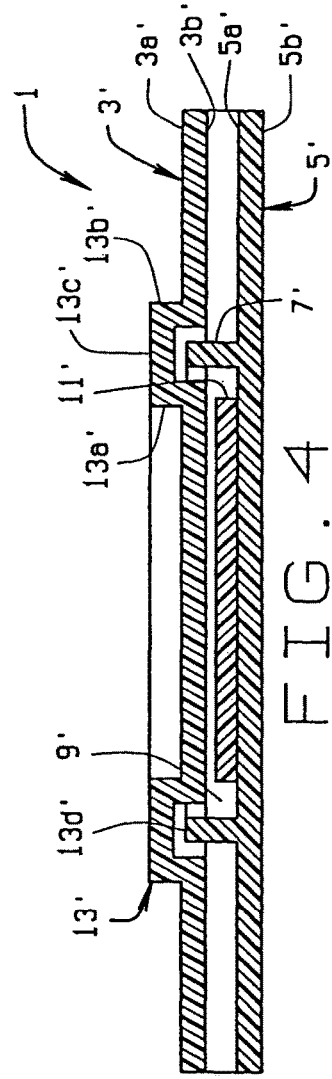
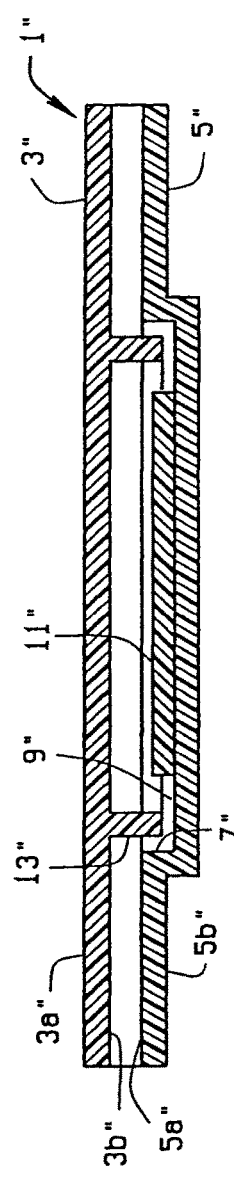
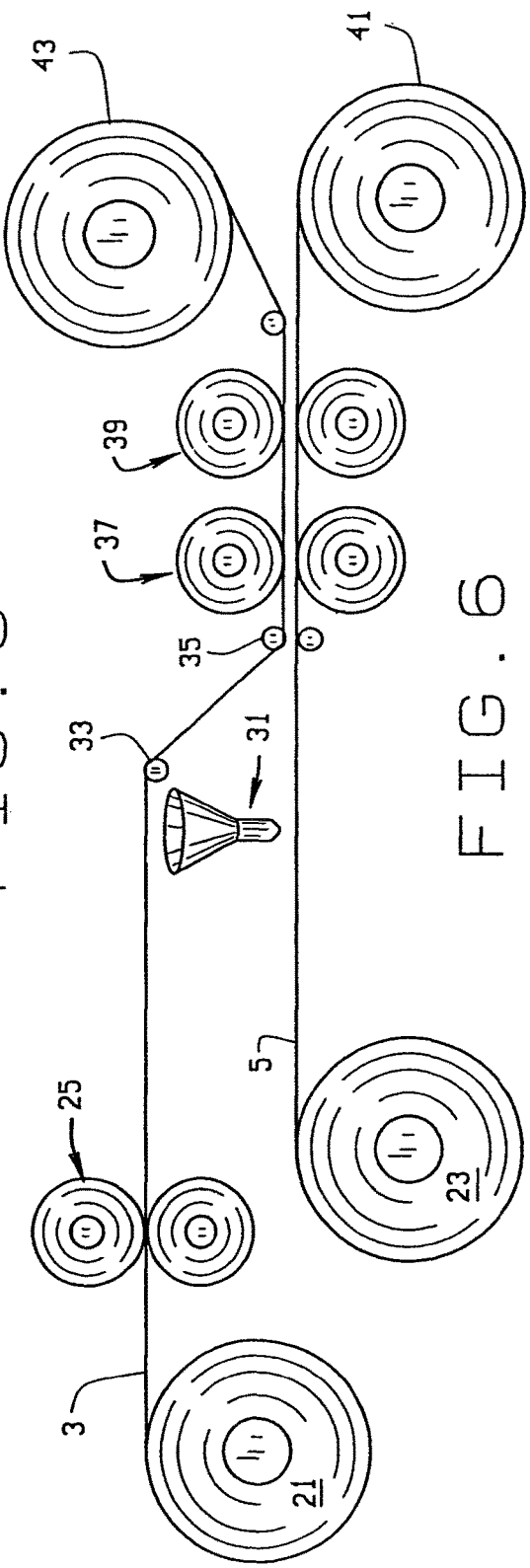
FIG. 4
FIG. 5
FIG. 6

FRAGRANCE SAMPLER INSERT

CROSS-REFERENCE TO RELATED APPLICATIONS

This is a continuation-in-part of co-pending application having Ser. No. 10/464,392, which was filed on Jun. 17, 2003 now abandoned, which is a continuation-in-part of Ser. No. 10/233,136, filed on Aug. 30, 2002 now U.S. Pat. No. 8,003,116, which in turn is a continuation-in-part of application having Ser. No. 09/858,566 filed on May 17, 2001, now U.S. Pat. No. 6,461,620, which, in turn, is a continuation-in-part of application Ser. No. 09/531,296 filed on Mar. 20, 2000, now U.S. Pat. No. 6,251,408, all of which are entitled Fragrance Sampler Insert, and all of which are incorporated herein by reference.

BACKGROUND OF THE INVENTION

This sampler relates to mail pieces inserted in magazine or direct mailpieces in general and more specifically to an absorbent applicator. A unique aspect of the present insert is an absorbent applicator attached to one of the plies of an insert.

Traditionally fragrance samplers were dry pre-scented blotter cards that had to be individually overwrapped to contain the fragrance for use in direct mail or magazine advertising. Beginning in the late 1970's, the micro-encapsulated Scentstrip® style magazine and direct mail insert was introduced. The Scentstrip insert is described in U.S. Pat. No. 5,093,182 to Ross. This product was produced on wide web offset printing equipment and therefore offered significant cost efficiencies for mass marketing. However, this was still a dry sample since the water moisture in the deposited fragrance slurry would very quickly wick into the paper substrate and leave the product sample dry. In fact, the entire technology depended on this moisture wicking since the wet microcapsules would not bond to the paper and would not break upon opening of the sampler. The microcapsules only break and release the fragrance oil when they are dry and are bonded to the paper. The draw back with this product was that it did not replicate the actual wet perfume product very well. In order to sample the fragrances in its real life wet form, the moisture wicking of the wet fragrance slurry deposited in the wide web offset printing process needed to be prevented. This was most easily accomplished by using existing narrow web flexographic label printing technology to create a pressure sensitive product that incorporated a wet fragrance or cosmetic sample material between impervious barrier materials such as plastic films and foil structures.

Currently there are three main fragrance sampler patents that guide us in wet fragrance or cosmetic sampling in magazines and direct mail. One is U.S. Pat. No. 5,391,420 to Bootman, which describes a pressure sensitive label comprising two plies of a film or plastic material: one bottom pressure sensitive ply, a deposit of fragrance material and an overlay of a second ply which traps the fragrance deposit. The sealing is by heat seal. The draw back of this product is that the fragrance material is often forced into and through the seal areas under pressure from the stacking forces of many magazines or inserts in distribution.

U.S. Pat. No. 5,161,688 to Muchin perfects upon the Bootman product by introducing a center ply material which has a die-cut window. This window ply is introduced onto the bottom pressure sensitive ply and thus creates a well for the fragrance material. The top, third ply is then added and the result is that stacking forces are distributed on to the widow ply and the fragrance material is exposed to less forces that may lead to seal failures and leakage: a major defect in the original product.

A modification of this second patent concept is described in U.S. Pat. No. 5,622,263 to Greenland. Greenland uses a liquid polyethylene or other hot liquid plastic material that creates the above-mentioned well and also assists in the heat sealing process. The draw back of the Muchin patent is that the additional window ply involves additional cost and manufacturing complications for die-cutting and introducing the third ply in the process. The Greenland concept also adds additional material cost and slows the process as the liquid plastic material needs to be deposited and bonded to the top and bottom ply. Further, the hot liquid plastic material introduces foreign odor and can, in some circumstances, contaminate the cosmetic or fragrance sampling material.

There are various other patents that deal with cosmetic sampling. Gunderman (U.S. Pat. No. 5,690,130) discloses a sampling device with a unit dose of cosmetic that is screen printed onto a base paper with a perimeter adhesive and clear film overlay. In this case a well area is embossed to receive an integral applicator. The well is not designed as a receptor for the cosmetic product nor is the embossing incorporated into the seal so as to afford strength and allow the seal to withstand pressure better. Also, this sampler uses screen printing and, as disclosed, is not intended or capable of delivering a wet liquid dose of cosmetic material. Lastly, a pressure sensitive base material is not envisioned which would allow automatic affixing as a label onto magazine or direct mail materials as the current Invention envisions.

Gunderman (U.S. Pat. No. 5,566,693) describes a screen printed sampler that delivers a cosmetic dose under a clear film overlay with pressure sensitive base material allowing affixing as a label. Again, this sampler is not designed to deliver a wet fragrance. The fragrance formulation requires fragrance to be mixed in a powder-based vehicle so that it can be screen printed. Also the sealing is not designed to contain wet fragrance or provide enough strength to contain liquid under stacking pressure. Further no embossing is envisioned to hold a cosmetic dose or to create seal wall integrity.

Gunderman (U.S. Pat. No. 5,562,112) envisions a lipstick sampler, again with neither a well or an embossed seal wall feature.

Ashcraft (U.S. Pat. No. 5,249,676) describes a multi-layer film with a flavor carrier layer between barrier layers. This does not create a wet fragrance sampler and there is no provision to create seals by embossing or otherwise that will allow a wet cosmetic sample to be contained under pressure.

Moir (U.S. Pat. No. 5,192,386) describes a screen printed, two-ply sampler with perimeter adhesive and clear film overlay. The cosmetic ingredient is a cosmetic powder, a heated oily, non-liquid waxy material, or a fragrance in a dry powder formulation. The product is dry, not wet, and there is no provision for creating heat sealed, embossed or interlocking walls to define a well and create internal seal strength sufficient to withstand stacking forces.

Szycher et al. (U.S. Pat. No. 4,880,690) shows a perfume patch.

Moir (U.S. Pat. No. 4,848,378) discloses a cosmetic screen printed, two-ply sampler that allows a pattern deposit of the cosmetic ingredient in the form of a non-smeary powder. This product is not pressure sensitive has no embossed wells or seal walls and does not deliver a wet sample.

Dreger (U.S. Pat. No. 4,769,264) discloses a label product comprising at least two sheets, bonded by adhesive, with microencapsulated fragrance. The liquid fragrance inside the microspheres is so little that it does not create a wet rendering of the product and is as dry to the touch and in current day dry "scents/rips". There is no mention of creating a well to hold the cosmetic dose in a confined area, nor is any use made of embossing or interlocking seal walls to create an improved seal and resist stacking pressure.

Moir (U.S. Pat. No. 4,751,934) discloses another version of a screen printed cosmetic powder formulation that may include fragrance in a two-ply pressure sensitive label construction. The seals of the two ply layers are by adhesive seal and the product rendering is dry or waxy, as in the lipstick dose version, but not wet as contemplated in the current invention. No embossing or debossing is used to create well areas or build wall seals.

Fraser (U.S. Pat. No. 4,720,423) describes using in a multi-layer strip having an adhesive with frangible microcapsules as a package overwrap. This product does not render a wet sample and create wells or seal walls either.

Charbonneau (U.S. Pat. No. 4,606,956) discloses a pressure sensitive two ply label construction with conventional microencapsulated slurry applied wet and then allowed to dry as is the conventional practice in the manufacture of scent strips. The product sample is rendered in a dry state, no wells or embossed walls are used to create a more impervious seal that can hold up to stacking forces.

There are several other patents that disclose fragrance samplers. Charbonneau (U.S. Pat. No. 4,606,956) shows an on page fragrance sampling device. Charbonneau (U.S. Pat. No. 4,661,388) shows a pad fragrance sampling device. Fraser (U.S. Pat. No. 4,720,423) shows a package opening system. Moir et al. (U.S. Pat. No. 4,751,934) discloses a cosmetic sampler. Dreger (U.S. Pat. No. 4,769,264) discloses an on page fragrance sampling device. Moir et al. (U.S. Pat. No. 4,848,378) discloses a cosmetic sampler. Moir et al. (U.S. Pat. No. 5,192,386) discloses a method of making a cosmetic sampler. Ashcraft et al. (U.S. Pat. No. 5,149,676) discloses a flavor burst structure and method of making it. Gundermann (U.S. Pat. No. 5,562,112) discloses a lipstick sampler. Gundermann (U.S. Pat. No. 5,566,693) discloses a fragrance sampler. Gundermann (U.S. Pat. No. 5,690,130) discloses a cosmetic sampler with an integrated applicator. Sweeny (U.S. Pat. No. 4,493,869) discloses fragrance microcapsules clear substrate. Turnbull (U.S. Pat. No. 4,487,801) discloses a fragrance releasing pull-apart sheet. Greenland (U.S. Pat. No. 5,622,263) discloses a sampler package and method of making it. Muchin (U.S. Pat. No. 5,161,688) discloses a sampler and method of making the sampler. Bootman (U.S. Pat. No. 5,391,420) discloses fragrance laden pouch samplers.

Greenland (U.S. Pat. No. 5,879,769) describes a three ply sampling product that creates a well. The well forms by placing two flat plies upon the top of a base window of die cut material. This is in contrast to Muchin '688 that had disclosed the window die cut between two solid plies.

Wilkman (U.S. Pat. No. 6,305,531 and applications 2002/0011424, 2003/0106812) describes a fused applicator that has a strap or pouch upon the bottom ply. The strap or pouch holds a ply upon the applicator. The applicator lacks pressure sensitivity and poorly affixes onto a mailer card or a magazine page.

Arcade Marketing, Inc. (Liqua Touch product) describes a non-woven material swatch placed between two plies of material. The swatch detaches from the sampler and a person may use the swatch as an applicator. In use, a person touches the cosmetic or fragrance contained upon the swatch. However, the present invention fuses a swatch to the top ply. Using the present invention, a person handles the swatch without skin contact and contamination of the sample.

BRIEF SUMMARY OF THE INVENTION

Briefly stated, a sampler is provided for insertion into an article such as a magazine or a mass mailing. The sampler includes a bottom ply and a top ply, both of which have an upper surface and a lower surface. A well is formed in at least one of the top and bottom plies to receive the sample. The well can be formed by a wall on the bottom ply, or can be formed as a depression in the bottom ply. A cosmetic sample (such as a wet fragrance sample) is deposited on the bottom ply. An absorbent applicator attaches to the top ply. The top ply and bottom ply are connected together to form a seal to substantially prevent leakage of the sample. A barrier formation can be formed in the bottom ply, positioned within the area defined by the wall, and sized and shaped to impede the flow of the sample on the bottom ply. For example, the barrier formation can comprise a plurality of dimples, knurls, baffles, or grooves.

BRIEF DESCRIPTION OF THE DRAWINGS

FIG. 4 is a cross-sectional view of an alternative construction of the fragrance sampler;

FIG. 5 is a cross-sectional view of another alternative construction of the fragrance sampler;

FIG. 6 schematic drawing of an alternative process for producing the sample of either FIG. 2 or 4;

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

Figure 1:
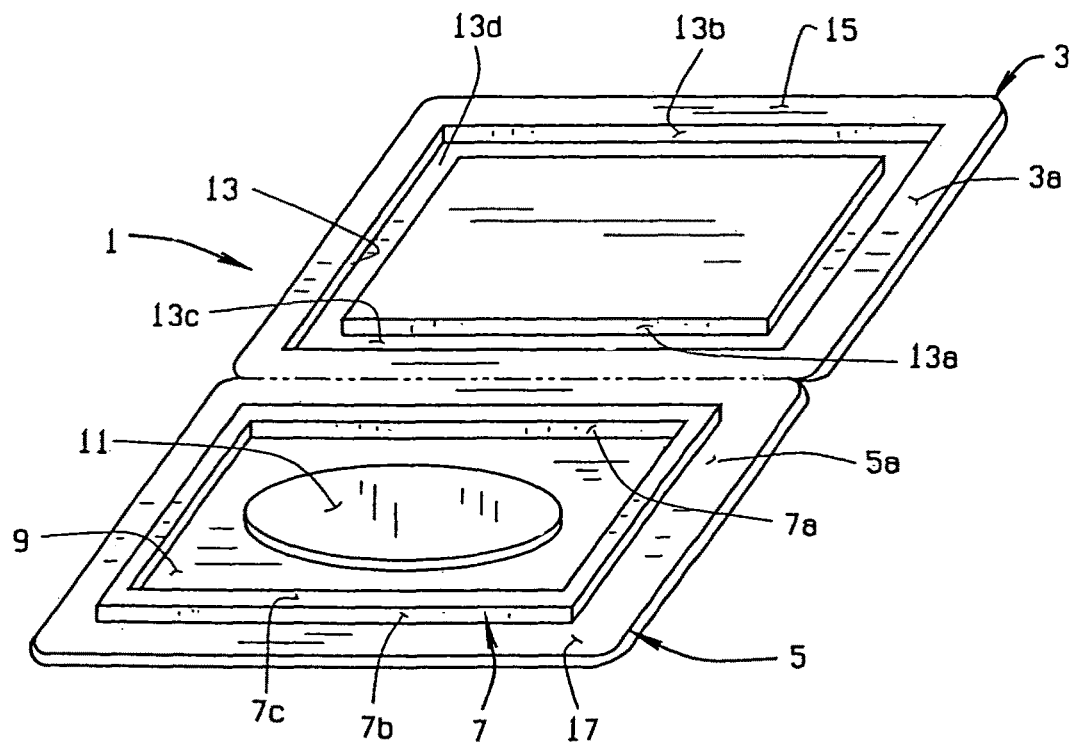
FIG. 1 is a perspective view of a fragrance sampler of the present invention prior to assembly of the sampler.
Figure 2:
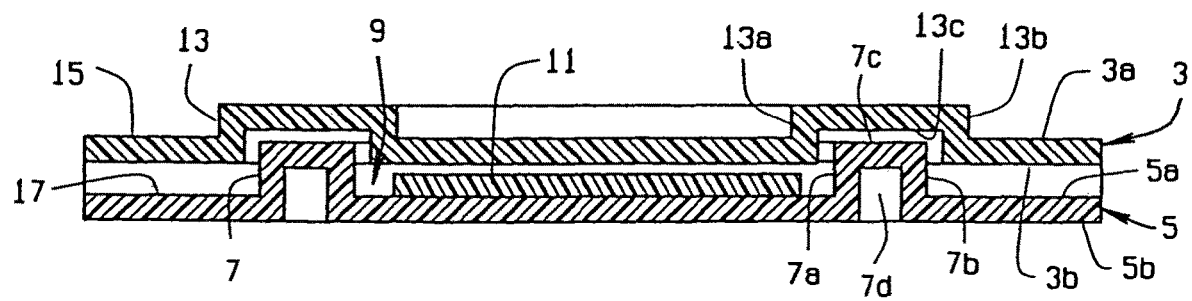
FIG. 2 a cross-sectional view of the sampler when assembled.

A first embodiment of a sampler 1 of the present invention is shown in FIGS. 1 and 2. The sampler 1 includes a top ply 3 and a bottom ply 5, both of which are preferably formed from a foil, a polyester, or a polyethylene laminated structure. The plies can alternatively be made of acetate or other paper, foil, and plastic film laminated or non laminated barrier plies. To facilitate affixing the sampler, for example, in a magazine or other publication, a pressure sensitive adhesive can be applied to either the top ply 3 or bottom ply 5 of the sampler.

The top and bottom plies 3 and 5 each include top and bottom surfaces 3a, 5a and 3b, 5b, respectively. A wall 7 is formed in the bottom ply 5 which extends up from the bottom ply's upper surface 5a. The wall 7, as shown, has an inner surface 7a, an outer surface 7b, and a top surface 7c which define a channel 7d in the bottom ply bottom surface 5b. The channel 7d is preferably rectangular in cross-section (but could have other configurations), and the wall 7 defines a "double wall." The wall 7 also defines a well 9 into which a wet fragrance sample 11 can be deposited. The fragrance sample 11 can be a sample of a perfume, or a cosmetic creme, lotion, hair color tint, lip stick, powder, or other cosmetic ingredient.

An opposing wall 13 is formed in the top ply 3 and extends upwardly from the top ply top surface 3a (with reference to FIG. 2). The wall 13 has an inner surface 13a, an outer surface 13b, and a top surface 13c which, in combination, define a channel 13d in the top ply bottom surface 3b (again, with reference to FIG. 2). The top ply channel 13d corresponds in shape to the bottom ply wall 7. As with the bottom ply channel 7d, the top ply channel 13d is preferably rectangular in cross-section (but could have other configurations that correspond to the configuration of the bottom ply channel 7d), and the wall 13 is a "double wall." As seen in FIG. 2, the wall 13 in the upper ply has dimensions slightly larger than the dimensions of the bottom ply wall 7, and the channel 13d is slightly wider than the channel 7d. Thus, the top ply wall 13 receives the bottom ply wall 7, as seen in FIG. 2, so that the walls 7a-c defining the lower ply channel 7d are substantially adjacent the walls 13a-c defining the upper ply channel 13d.

The top and bottom ply walls 7 and 13 are preferably formed by an embossing/debossing process.

As can be seen in FIGS. 1 and 2, when the walls 7 and 13 are formed, the top and bottom plies each include a frame 15, 17 surrounding the walls 7 and 13, respectively. The top ply 3 and bottom ply 5 are adhered together to cover and close the well 9 so that the sample 11 will be sealed in the well 9 between the two plies. The plies can be joined by heat sealing or sonically sealing the two plies together or using an adhesive to bond the top plies together. If an adhesive is used, the adhesive can be cationic cure coating adhesive, or other equally acceptable adhesive which will form a liquid tight barrier to prevent premature release of the fragrance contained in the well 9.

Although the walls 7 and 13 are shown in FIGS. 1 and 2 to be "double walls" with one wall being received in the channel of the other, one of the walls 7 and 13 could alternatively be formed as single walls as seen in the sampler 1' of FIG. 4. The sampler 1' includes a top ply 3' and a bottom ply 5'. The top and bottom plies 3' and 5' each include top and bottom surfaces 3a', 5a' and 3b', 5b'. A wall 7' extends up from the bottom ply's upper surface 5a'. Unlike the wall 7 of the sampler 1 of FIGS. 1 and 2, the wall 7' is a single wall. The wall 7' is spaced inwardly from the outer edge of the sampler bottom ply 5' and extends around the bottom ply 5' to form a well 9' into which a wet fragrance sample 11' can be deposited.

An opposing wall 13' extends up from the top ply top surface 3a'. The wall 13' has an inner surface 13a', an outer surface 13b', and a top surface 13c' which, in combination, define a channel 13d' in the top ply bottom surface 3b'. The top ply channel 13d' is sized to receive the bottom ply wall 7', so that the walls 7' and 13' are engaged when the sampler 1' is formed.

Another alternative construction for the fragrance sampler is shown in FIG. 5. In this construction, the sampler 1" includes a top ply 3" and a bottom ply 5" having upper and lower surfaces 3a", 5a" and 3b", 5b", respectively. Unlike the embodiments of FIGS. 1 and 4, the fragrance sampler 1" includes a well 9" formed in the bottom ply 5" which holds the fragrance sample 11". Unlike the wells of samplers 1 and 1' (FIGS. 1, 2, and 4) in which the wells are above or on top of the bottom ply, the well 9" is below the plane of the bottom ply 5". The well 9" can be formed by either an embossing or debossing process. The top ply 3" includes a wall 13" which extends from the top ply bottom surface 3b". The wall 13" is sized to be received in the well 9" so that, when the sampler 1" is formed, the wall 13" will be adjacent the wall 7" of the well 9" and so that the two walls will engage each other to form a liquid tight seal to retain the liquid fragrance sample in the well 9". Unlike the samplers 1 and 1' of FIGS. 1-4, the sampler 1" includes no "double walls", rather, both the walls 7" and 13" are single walls.

Figure 3:
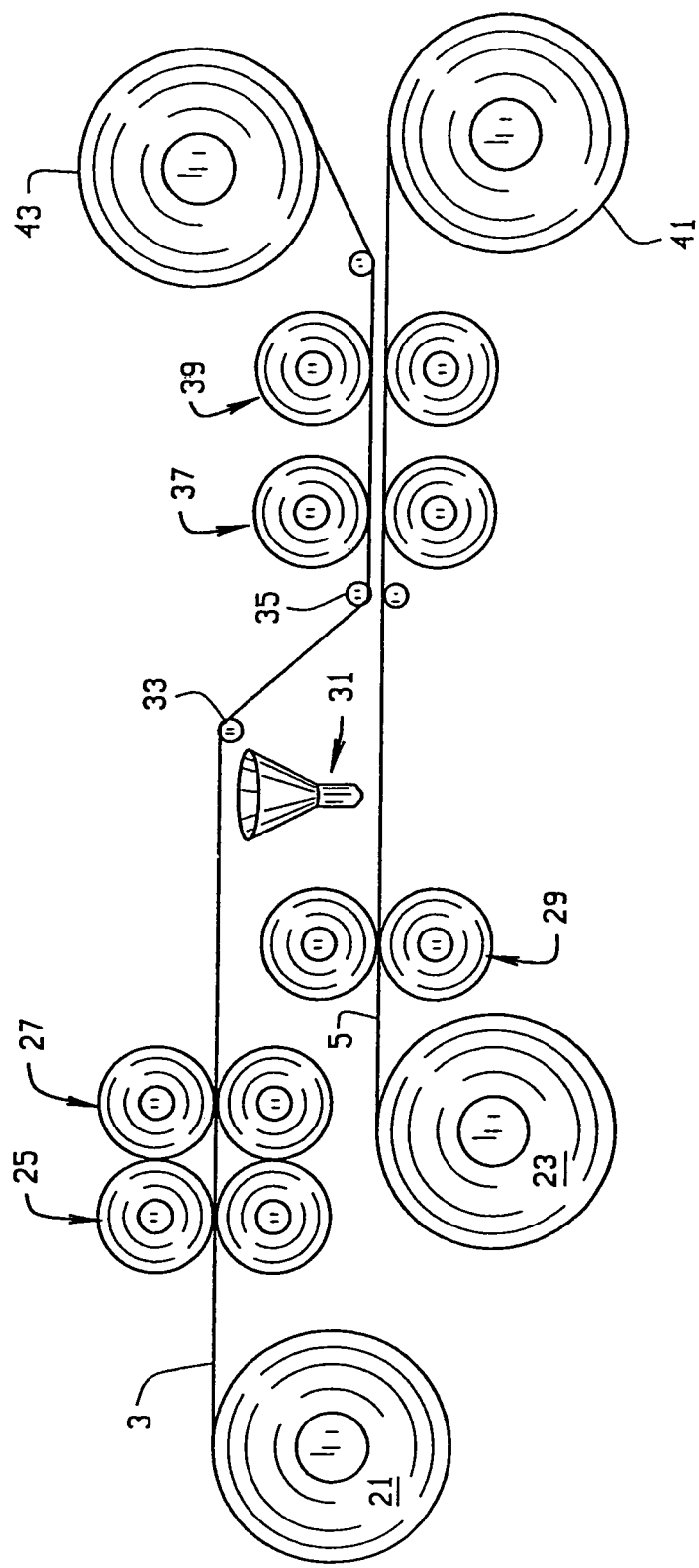
FIG. 3 is a schematic drawing of the sampler producing process.

The process for producing the samplers 1, 1', and 1" is shown schematically in FIG. 3. Webs of the top and bottom ply material are originally contained on rollers 21 and 23, respectively. The top ply material is pulled off the top ply roller 21 and passed through a printer station 25 and then through an embossing station 27. At the printer station 25 desired graphics are printed on the top surface 3a, 3a', 3a" of the top ply 3, 3', 3". The top ply wall 13, 13', 13" is formed at the embossing station 27. The top foil laminated ply is printed on a narrow web flexographic or letter press printing press, with all subsequent finishing steps performed either in-line or off-line.

While the top ply is being processed, the bottom ply material is pulled off the bottom ply roller 23 and passed through an embossing station 29 where the bottom ply wall 7, 7', 7" is formed. A flat bed embossing tool is used to push up or emboss the wall 7, 7', 7" on the bottom ply to form the well 9, 9', 9". The bottom ply embossing can be also be formed by rotary embossing methods.

The bottom ply 5, 5', 5" is passed under an injection station 31 where a liquid fragrance sample is deposited in the well 9, 9', 9". The sample 11, 11', 11" can be deposited in any other desired manner, such as extrusion, spray, flexographic equipment or silkscreen.

After the top ply has been printed and after the wall 13, 13', 13" is formed in the top ply, the top ply is passed about a pair of rollers 33 and 35 to bring the top ply 3, 3', 3" into close proximity with the bottom ply 5, 5', 5". The path of travel of the bottom ply is preferably substantially horizontal, at least after the fragrance sample has been deposited in the bottom ply well 9, 9', 9", to avoid spilling of the sample. Thus, the top ply 3, 3', 3" is preferably brought to the bottom ply 5, 5', 5". However, the process could be designed so that the bottom ply is brought up to the top ply. The two plies are then passed through a sealing station 37 where the two plies are adhered together to form a liquid tight seal which will contain the fragrance sample in the chamber. The sealing station interlocks with the well wall 7, 7', 7" with the top ply wall 13, 13', 13" to form a safe, closed well for the sample material. As can be appreciated, the webs of top ply and bottom ply material move at an indexed rate such that when the two plies are brought together at the sealing station, the top ply wall 13, 13', 13" will be in alignment with the bottom ply wall 7, 7', 7". The sealing station 37 is preferably is a heat sealer, and the top and bottom plies can be adhered or sealed together for example, by welding (such as friction, sonic, or ultrasonic welding), or other standard heat sealing processes which will create a seal between the two plies. Alternatively, as noted above, the sealing station can utilize an adhesive, such as cationic cure coating adhesives, traditional cohesive seals, or adhesive seals, which will bind the top and bottom plies together to form the seal.

The joined plies are then passed to a die-cut station 39 where side portions of the frames 15 and 17 are removed from the formed samplers. The die-cutting step can be performed with either rotary or flat bed equipment. The formed samplers are then collected on a product roller 41. Product is delivered in roll form for automatic applications to other printed materials. The die-cutting station 39 can also form perforations between adjacent samplers to facilitate separation of the samplers. The waste material can be collected on a waste roller 43.

If desired, a pressure sensitive material with a release liner can be incorporated into the bottom ply so as to result in a product that can later be readily applied to another substrate using affixing equipment. Alternatively, the pressure sensitive adhesive with its release liner can be applied to the bottom layer ply. The pressure sensitive adhesive can be applied to the bottom ply either as a pre-treatment or after the embossing/debossing process.

An alternative production process is shown in FIG. 6. As with the process of FIG. 3, webs of the top and bottom ply material are originally contained on rollers 21 and 23, respectively. The top ply material is pulled off the top ply roller 21 and passed through a printer station 25 where desired graphics are printed on the top surface of the top ply. At the same time, the bottom ply material is pulled off the bottom ply roller 23 under an injection station 31 where a liquid fragrance sample is deposited on the bottom ply. As can be appreciated, in this version, the liquid fragrance sample is deposited on the bottom ply prior to the formation of the walls of the top and bottom plies.

After the top ply has been printed, the top ply is passed about a pair of rollers 33 and 35 to bring the top ply into close proximity with the bottom ply. The path of travel of the bottom ply is preferably substantially horizontal, at least after the fragrance sample has been deposited on the bottom ply to avoid spilling of the sample. Thus, the top ply is preferably brought to the bottom ply. However, the process could be designed so that the bottom ply is brought up to the top ply. The two plies are then passed through a sealing station 37. At the sealing station 37, the walls of the top and bottom plies are formed, and the two plies are adhered together to form a liquid tight seal which will contain the fragrance sample in the chamber. The sealing station interlocks with the well wall with the top ply wall to form a safe, closed well for the sample material. As can be appreciated, the webs of top ply and bottom ply material move at an indexed rate such that when the two plies are brought together at the sealing station, the fragrance will be within the walls formed at the sealing station and the printing on the top ply will be above the liquid fragrance sample. The sealing station 37 is preferably a heat sealer, which embosses/debosses the top and bottom ply walls in the sampler at the same time the sampler plies are heat sealed together.

The joined plies are then passed to a die-cut station 39 where side portions of the frames 15 and 17 are removed from the formed samplers. The die-cutting step can be performed with either rotary or flat bed equipment. The formed samplers are then collected on a product roller 41. Product is delivered in roll form for automatic applications to other printed materials. The waste material can be collected on a waste roller 43.

In another variation, the walls in the bottom ply can be "pre-formed" to allow for filling of the well in an off-line operation.

As can be appreciated, the sampler of the present invention is easily formed from only two plies of material. The top and bottom ply walls are substantially adjacent each other, to engage each other to form a liquid tight seal around the fragrance sample. Additionally, the adjacent walls will reinforce each other to enable the walls to carry the stacking or compression forces to reduce seal failures and fragrance leaks.

Figure 7A:
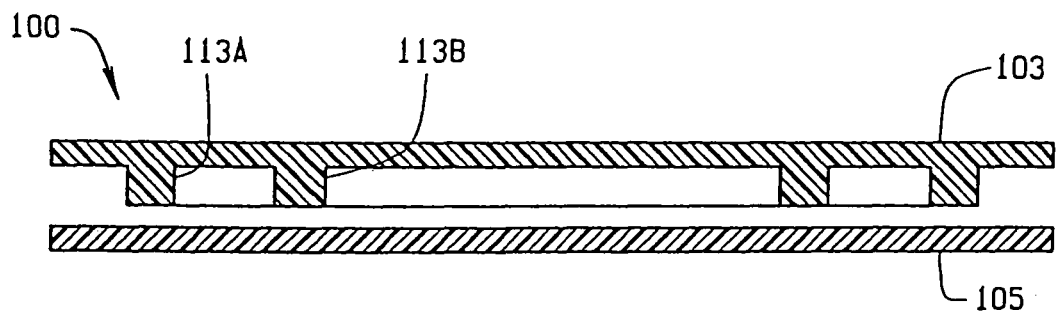
FIGS. 7A-C show three alternative constructions of the fragrance sampler which include single walls.

Several different alternative configurations of the fragrance sampler are shown in FIGS. 7A-9D. In FIG. 7A, the fragrance sampler 100 has a top ply 103 and a bottom ply 105. The bottom ply 105 is flat. That is, it does not include any walls or wells which define a chamber. Rather, the top ply has a pair of spaced apart walls 113A and 113B which are concentric with each other, and which extend downwardly from the bottom surface of the top ply. The sampler 100 is formed in substantially the same way as described above, with the fragrance sample being deposited on the bottom ply 105 in an area which will be surrounded by the wall 113B, so as to be contained within the sampler upon sealing of the sampler. As can be appreciated, the two plies can be reversed, so that the walls 113A, B form a chamber into which the fragrance sample is deposited during formation of the sampler. In this case, the well will be formed in the bottom ply, and the top ply will be flat. The top ply will then be sealed (such as by heat sealing) to the bottom ply to form a liquid tight seal between the two plies.

Figure 7B:
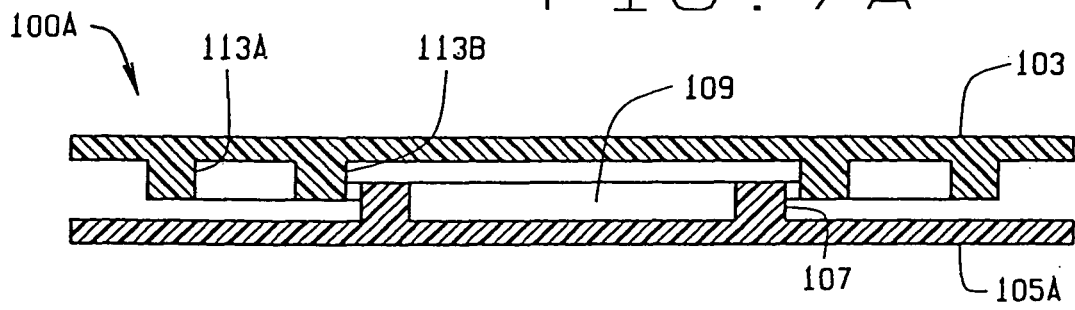

The sampler 100A shown in FIG. 7B includes the top ply 103 identical to the top ply 103 of the sampler 100 (FIG. 7A), and a bottom ply 105A. The bottom ply includes a single wall 107 which extends upwardly from the upper surface of the bottom ply to define a fragrance chamber 109. The bottom ply wall 107 is positioned to be contained within the top ply wall 113B, and sized so that its outer surface will abut the inner surface of the top ply wall 113B. Thus, the walls 107 and 113B will effectively engage each other when the sampler is sealed.

Figure 7C:
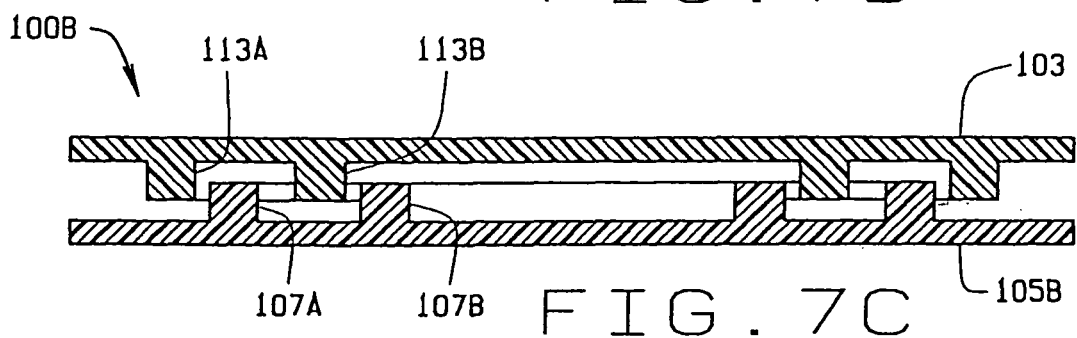

The sampler 100B shown in FIG. 7C includes the top ply 103 identical to the top ply 103 of the sampler 100 (FIG. 7A), and a bottom ply 105B. The bottom ply 105B includes a pair of spaced apart walls 107A and 107B which are concentric with each other, the wall 107B being contained within the wall 107A. As seen, the top ply walls and bottom ply walls are sized to be off-set from each other, such that the bottom ply wall 107A is received between the top ply walls 113A and 113B; and the bottom ply wall 107B is received inwardly of the top ply wall 113B. Thus, the walls 113A, B and 107A, B mesh with each other.

Figure 8A:
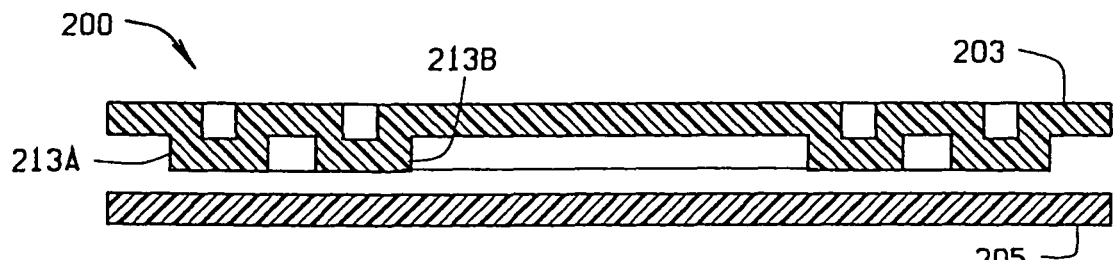
FIGS. 8A-B show two other alternative constructions of the fragrance sampler which include double walls.
Figure 8B:
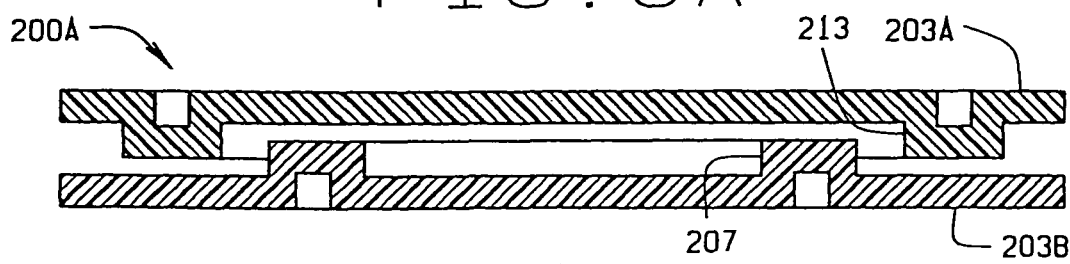

The samplers 100, 100A, and 100B all include single walls, as opposed to double walls, such as the walls 7 and 13 of the sampler 1 (FIG. 2). The samplers 200 and 200A shown in FIGS. 8A and 8B, respectively, include only double walls. The sampler 200 (FIG. 8A) includes a top ply 203 and a bottom ply 205. The bottom ply 205 is identical to the bottom ply 105 (FIG. 7A); it is flat and has no walls, wells, etc. The top ply 203 includes a pair of double walls 213A and 213B which are concentric with each other, the wall 213B being formed within the wall 213A. As seen in FIG. 8A, the concentric double walls, which are adjacent each other, give the top ply a crenelated appearance. As can be appreciated, the sampler 200 is similar to the sampler 100, except that the single top ply walls 113A, B of the sampler 100 have been replaced with the double walls 213A, B. Hence, the sampler 200 would be formed substantially the same way as the sampler 100. As with the sample 100, the sampler 200 could be formed such that the walls are formed in the bottom ply to define a well into which the sample is deposited. The top ply would then be flat. After the sample is deposited in the well, the two plies are brought together, as discussed above, to adhere the two plies together to form a liquid tight seal between the two plies.

The sampler 200A (FIG. 8B) is somewhat similar to the sampler 1 (FIG. 2). It includes a top ply 203A and a bottom ply 203B. The top ply 203A includes a double wall 213 which extends downwardly from the top ply's bottom surface. The bottom ply includes an upwardly extending wall 207. In the sampler 1 the wall 7 is received in the channel defined by the wall 13. In the sampler 200A, the respective location of the bottom ply wall has been moved relative to the top ply wall, so that the outer surface of the bottom ply wall 201 is adjacent the inner surface of the top ply wall 213 when the sampler is formed.

Figure 9A:
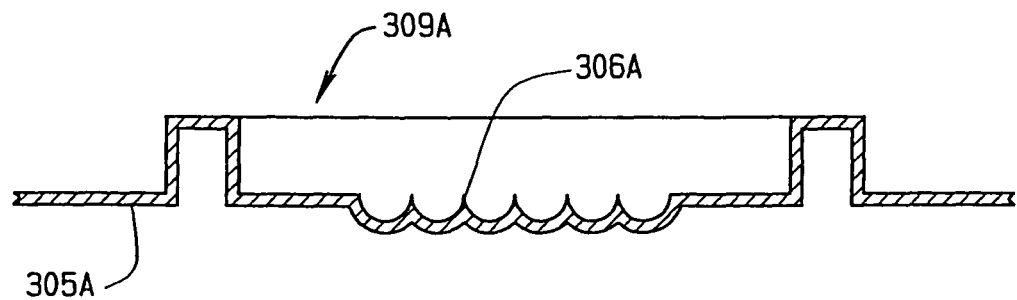
FIGS. 9A-D show alternative constructions of the sampler bottom ply, wherein the bottom ply is provided with flow barriers.
Figure 9B:
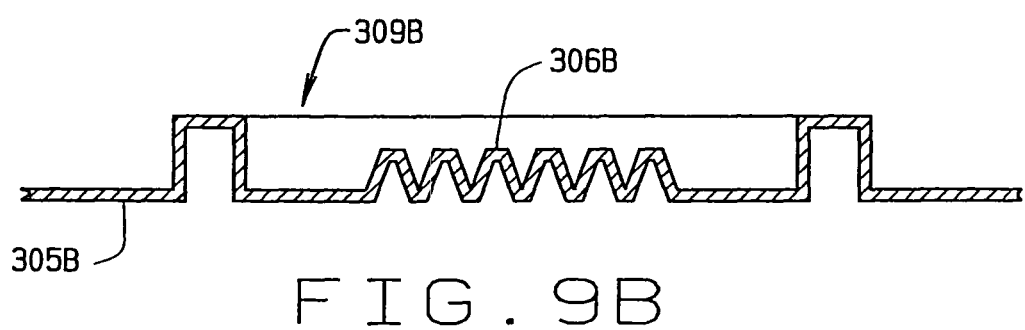
Figure 9C:
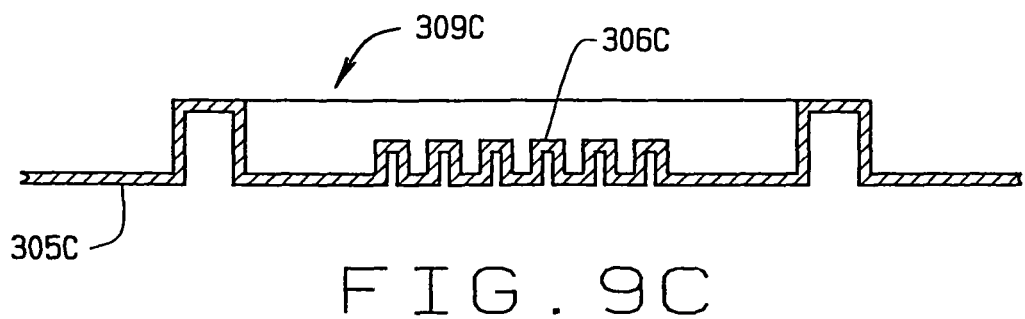
Figure 9D:
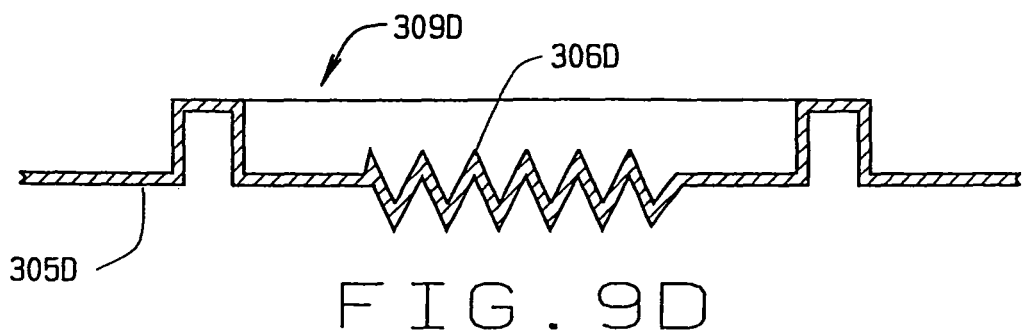

FIGS. 9A-9D show various alternative configurations to the wells 309A-D in the bottom plies 305A-D. In FIG. 9A, the well 309A is provided with a bottom surface having dimples 306A. The dimples are preferably formed in a desired pattern in the bottom of the well 309A. In FIG. 9B, the well 309B is provided with knurls 306B in the bottom surface of the well. In FIG. 9C, the well 309C is provided with baffles 306C in the form of crenellations which extend across the well. And, in FIG. 9D, the well 309D is provided with triangular grooves or hatches 306D in the bottom surface of the well. In each of the bottom plies 305A-D, the formations 306A-D in the bottom surface of the well provide barriers to the flow of the wet sample which is deposited in the well. The four formations shown are illustrative only, and other types of formations which will impede the flow of a wet sample can also be used. The barriers shown in FIGS. 9A-D can be incorporated into any of the samplers discussed above. The barriers can be formed in any desired manner, but are preferably formed in the same manner that the top and bottom ply walls are formed.

Figure 10:
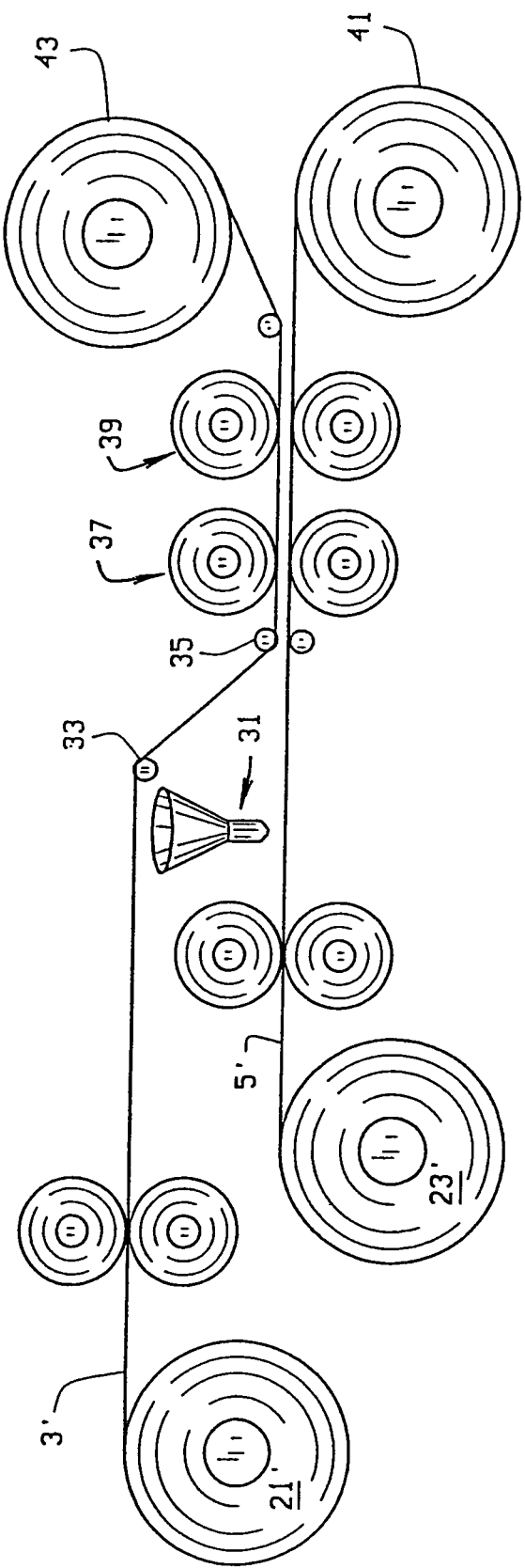
FIG. 10 is a schematic view of an alternative process for manufacturing the sampler.

FIG. 10 shows a method, somewhat similar to the method of FIG. 6, for producing the samplers. In this method, the top and bottom plies are pre-formed—that is, the various walls in the top and bottom plies are formed in a first operation to form a continuous web of sampler top and bottom plies. The two webs are formed onto rolls 21' and 23' from which the webs 3' and 5' are pulled. As can be appreciated, the two webs 3' and 5' threaded into the machinery, such that when they are brought together at the sealing station 37, the two plies will be in register. Prior to reaching the sealing station, the bottom ply 5' is brought past the injection station 31 where the sample is injected onto the ply 5'. The web 5' is threaded into the machinery so that the sample will be deposited in the well of the bottom ply (if the well is preformed). The web then passes through the cutting stating 39 where the sealed web is either perforated, or cut, to produce separable (or separated) samplers which can then be inserted in a magazine, mailer, etc.

Figure 11:
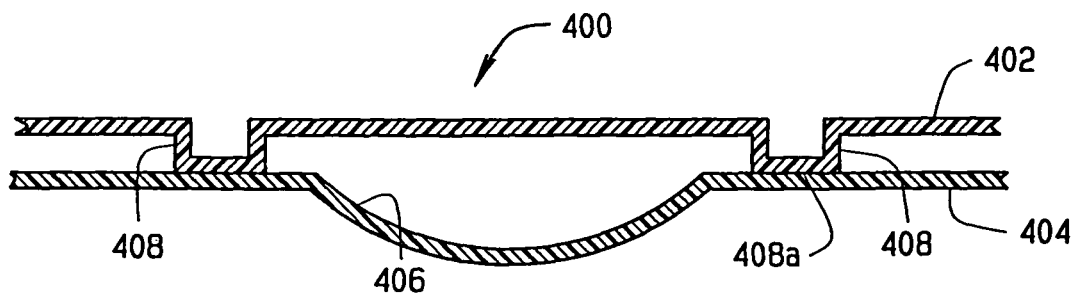
FIG. 11 is a cross-sectional view of a further embodiment of the sampler which is similar to the sampler of FIG. 5, but which lacks the interlock feature of the sampler of FIG. 5.

The samplers of FIGS. 1-9D all include interlocking walls, as described above. The samplers of FIGS. 11-14, on the other hand, do not have interlocking walls. The sampler 400 of FIG. 11 is similar to the sampler 1" of FIG. 5. The sampler 400 includes a top ply 402 and a bottom ply 404. Like the bottom ply of the sampler 1", the bottom ply 404 has a well 406 that is formed in the bottom ply by an embossing or debossing procedure. The well 406 is below the plane of the bottom ply 404, and is shown to be generally concave and curved (as opposed to rectangular). The top ply 402 includes a wall 408, which is shown to be a double wall similar to the wall 13 of the sampler 10 (FIG. 1) However, the wall 408 is positioned such that its inner surface is approximately aligned with the periphery of the well 406. Thus, the bottom surface 408a of the wall will contact the upper surface of the bottom ply 404. The sampler 400 can be formed using any of the methods described above. The sample will be received in the well 406, and, in a subsequent step, the wall bottom surface 408a will sealed to the bottom ply top surface to form a liquid tight seal around the well. The seal between the wall bottom surface and the bottom ply top surface can be formed in any number of ways. For example the seal can be formed by welding (such as heat welding, sonic welding, ultrasonic welding, friction welding, etc.) or by bonding using adhesives.

Figure 12:
FIG. 12 is a cross-sectional view of yet another embodiment of the sample in which walls on the top and bottom plies are aligned, and thus, the sampler lacks the interlock feature.
Figure 13:
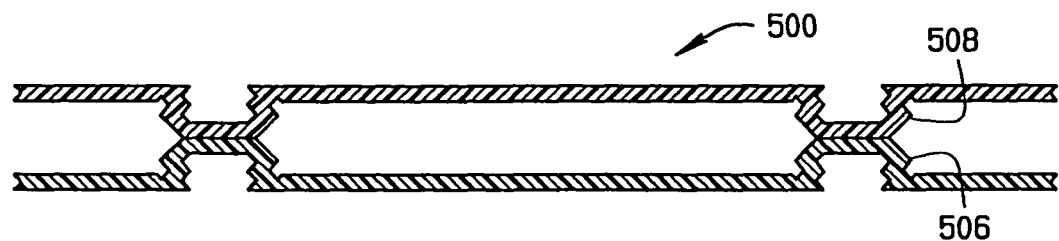
FIG. 13 is a cross-sectional view of the sampler of FIG. 12, but with the embossed walls in a collapsed condition.

The sampler 500 of FIG. 12 includes bottom and top plies 502 and 504. Walls 506 and 508 are formed on the bottom and top plies, respectively, such that the walls face each other. Hence, the bottom ply wall 506 is formed on the upper surface of the bottom ply and the top ply wall 508 is formed on the bottom surface of the top ply. The walls 506 and 508 are shown to be double walls, but could be single walls if desired. As can be seen, the walls 506 and 508 are aligned with each other, such that their respective end surfaces 506a and 508a will contact each other when the two plies are brought together. Because the walls 506 and 508 are aligned, the sampler 500 lacks the interlocking feature of the sampler 10 (FIG. 1), for example. However, the two plies are joined together at the walls to form a liquid tight seal between the top and bottom plies. The seal between the wall bottom surface and the bottom ply top surface can be formed in any number of ways. For example the seal can be formed by welding (such as heat welding, sonic welding, ultrasonic welding, friction welding, etc.) or by bonding using adhesives. The use of double walls facilitates welding of the two plies together. Upon completion of assembly of the sampler, the top and bottom ply walls 506 and 508 are crushed together, as seen in FIG. 13. When collapsed, the walls do not return to their original flat surface configuration. Rather, they form a physical wall barrier that provides additional compression resistance to the finished product.

Figure 14:
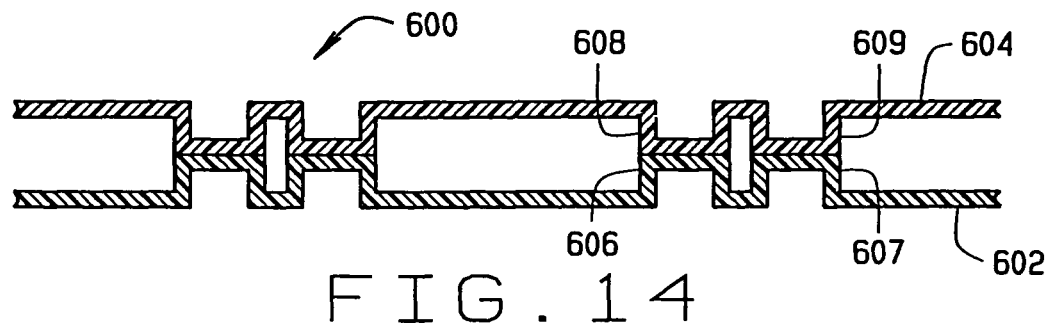
FIGS. 14 and 15 are cross-sectional view of a sampler similar to the sampler of FIGS. 12 and 13, but which has a double wall construction, rather than a single wall construction.
Figure 15:
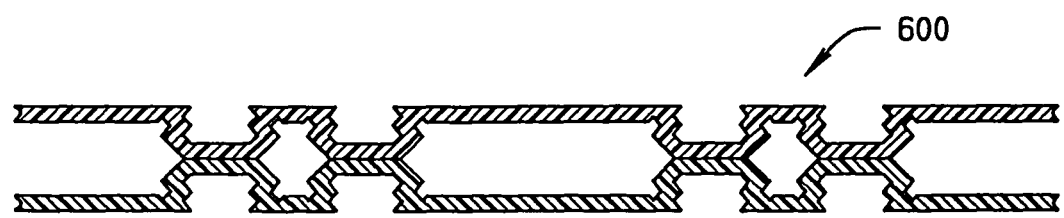

The sampler 600 shown in FIGS. 14 and 15, is substantially similar to the sampler 500. However, the sampler 600 is provided with two walls 606 and 607 on the bottom ply 602 and two wall 608 and 609 on the top ply 604. The walls 607 and 609 are outer walls which surround walls 606 and 608, which are inner walls. Like the sampler 500, the walls of the sampler are aligned with each other. Thus, the wall 606 and 608 are aligned and the walls 607 and 609 are aligned. The top and bottom plies 602 and 604 are assembled together in the same manner as the plies of the sampler 500, and, upon assembly, the walls 606-609 are crushed or collapsed, as seen in FIG. 15.

Figure 16:
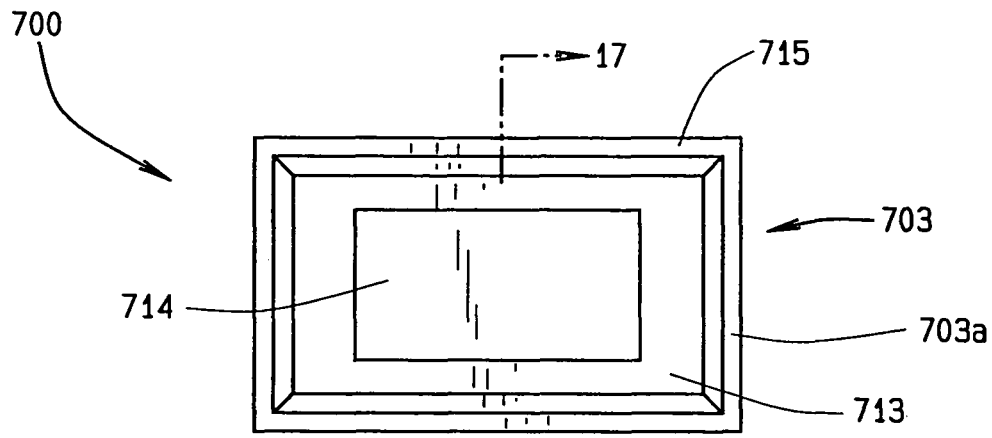
FIG. 16 is a top view of a sampler with an applicator attached to one ply.
Figure 17:
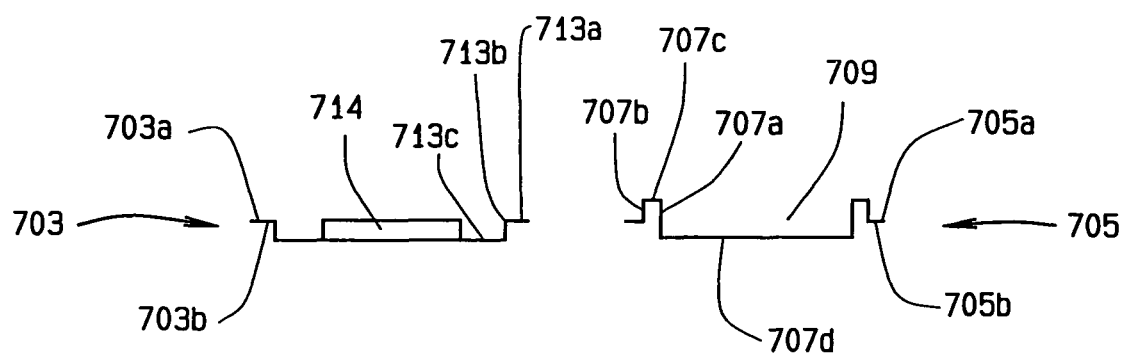
FIG. 17 is a sectional view of the sampler with an applicator attached to one ply of the present invention.

Another embodiment of a sampler 700 of the present invention is shown in FIGS. 16 and 17. The sampler 700 has similarities with the sampler 1. The sampler 700 includes a top ply 703 and a bottom ply 705, that each include top and bottom surfaces 703*a*, 705*a* and 703*b*, 705*b*, respectively. A wall 707 is formed in the bottom ply 705 upwardly from the upper surface 705*a*. The wall 707, as shown, has an inner surface 707*a*, an outer surface 707*b*, and a top surface 707*c* which define a channel 707*d* in the bottom surface 705*b*. Preferably, the channel 707*d* has a rectangular cross-section with radiused, or curved corners. The wall 707 along three or more edges of the sampler 700 defines a well 709 into which a wet fragrance sample 11 can be deposited, such as a perfume, a cosmetic creme, lotion, hair color tint, lip stick, powder, or other cosmetic ingredient. Further, the bottom ply 705 can incorporate a pressure sensitive construction rendering the sampler 700 in label form for affixing onto mailing cards or magazine inserts.

The top ply 703 engages the wall 707 and corresponds in shape to the bottom ply 705. A channel 713 forms in the top ply 703 which extends below the top surface 703*a*. The channel 713 has a top surface 713*a*, an inner surface 713*b* perpendicular to the top surface 713*a*, and a base surface 713*c* parallel and offset beneath the top surface 713*a*. The channel 713 has a generally rectangular symmetric cross section as in FIG. 17 on the left. The base surface 713*c* has an attached applicator 714. The applicator 714 has less height than the combined inner surfaces 713*b*, 707*a* and a width and a length to fit within the channel 713 and well 709. The applicator 714 has a construction of cellulose, organic, or similar non-woven fabric type material. The applicator 714 absorbs water, alcohol, oil, and the like based cosmetics.

As seen in FIG. 17, the channel 713 in the upper ply 703 has dimensions slightly larger than the dimensions of the wall 707, and the channel 713 is slightly wider and longer than the well 709. The base surface 713*c* has a width and a length to receive the wall 707 from the bottom ply 705 much like a cap. As the top ply channel 713 receives the bottom ply wall 707, the surfaces 707*a, b, c* defining the lower ply channel 707*d* are substantially adjacent to the surfaces 713*a, b, c* defining the upper ply channel 713.

As can be seen in FIGS. 16 and 17, when the wall 707 and channel 713 are formed, the top and bottom plies 703, 705 each include a frame 715, 717 surrounding the channel 713 and wall 707, respectively. The top ply 703 and bottom ply 705 are adhered together upon frames 715, 717 to cover and close the well 709 so that the sample 11 and applicator 714 will be sealed in the well 709 between the two plies 703, 705. The plies can be joined together by heat sealing or sonic sealing or by an adhesive bond. The adhesive can be cationic cure coating adhesive, or other equally acceptable adhesive which will form a liquid tight barrier to prevent premature release of the fragrance sample 11 contained in the well 709. The top ply channel 713 and bottom ply wall 707 are preferably formed by an embossing/debossing process. And, the applicator 714 permanently attaches to the channel 713 of the top ply 703 by adhesives, welding, fusing, or other means.

The bottom ply can incorporate a pressure sensitive construction rendering the sampler as a label for ease of affixing onto many cards or magazine inserts.

As various changes could be made in the above constructions without departing from the scope of the invention, it is intended that all matter contained in the above description or shown in the accompanying drawings shall be interpreted as illustrative and not in a limiting sense.

I claim:

1. A sampler for inserting into printed matter for a magazine or a mass mailing, the sampler including a bottom ply having a top surface and a bottom surface;
   a cosmetic sample;
   a well formed in said bottom ply to receive the flowable liquid cosmetic sample;
   a top ply having a top surface and a bottom surface;
   one or more embossed walls formed in at least the bottom ply;
   said embossed walls are one of single or double ply walls;
   a channel formed in the top ply;
   an absorbent applicator located within said channel and attached to said top ply, wherein said applicator remains uncompressed upon sealing said bottom ply to said top ply;
   said sampler including a frame upon said top surface of said bottom ply outside of said well, and a frame upon said top surface of said top ply outside of said channel, said frames sealing said applicator within said well in a liquid tight manner;
   said channel, said well, and said walls having a generally rectangular cross section and radiused corners;
   said well having a texture in the form of at least one of dimples, knurls, baffles, and grooves, to retain the flowable liquid cosmetics sample therein;
   said applicator being an absorbent fabric of one of cellulose, organic, or inorganic non-woven material, and said applicator joining to said top ply by one of welding, fusing, pressing, or gluing;
   said top ply and said bottom ply are a laminate of one of metal foil, polyester, or polyethylene;
   said top ply is symmetric to said bottom ply and said applicator at least partially fits within said well, said bottom ply has a pressure sensitive adhesive to connect said sampler to the printed matter, and said top ply and said bottom ply are embossed;
   wherein said well is a depression; said channel has dimensions at least as large as said well, such that said channel fits over said well and said walls fit within said channel;
   said bottom surface of said top ply adheres to said top surface of said bottom ply;
   whereby said channel, said walls, and said well when placed adjacent resist compression; and
   whereby said top ply abuts said bottom ply to form a liquid tight seal to prevent leakage of the sampler, and to impede the flow of the liquid cosmetic sample.

* * * * *